US008177785B2

(12) United States Patent
Vaidya

(10) Patent No.: US 8,177,785 B2
(45) Date of Patent: May 15, 2012

(54) METHOD FOR MINIMALLY INVASIVE TREATMENT OF UNSTABLE PELVIC RING INJURIES WITH AN INTERNAL ANTERIOR FIXATOR AND POSTERIOR ILIOSACRAL SCREWS

(76) Inventor: Rahul Vaidya, Tecumseh (CA)

( * ) Notice: Subject to any disclaimer, the term of this patent is extended or adjusted under 35 U.S.C. 154(b) by 662 days.

(21) Appl. No.: 12/287,280

(22) Filed: Oct. 9, 2008

(65) Prior Publication Data

US 2010/0094290 A1    Apr. 15, 2010

(51) Int. Cl.
*A61B 17/80* (2006.01)
(52) U.S. Cl. .................................. 606/60; 606/86 R
(58) Field of Classification Search ........... 606/60–75, 606/246–331
See application file for complete search history.

(56) References Cited

U.S. PATENT DOCUMENTS

| | | | |
|---|---|---|---|
| 2005/0277928 A1* | 12/2005 | Boschert | 606/61 |
| 2008/0108989 A1* | 5/2008 | Parsell et al. | 606/60 |
| 2010/0042149 A1* | 2/2010 | Chao et al. | 606/246 |

OTHER PUBLICATIONS

Gardner, Michael and Nork, Sean. "Stabilization of Unstable Pelvic Fractures with Supraacetabular Compression External Fixation." Journal of Orthopaedic Trauma 21.4 (2007): 269-273.*
Sciulli, Robert. "CT-Guided Iliosacral Screw Placement: Technique and Clinical Experience." American Journal of Roentgenology 188 (2007): W181-W192.*

* cited by examiner

*Primary Examiner* — Thomas C. Barrett
*Assistant Examiner* — Olivia C Chang
(74) *Attorney, Agent, or Firm* — David W. Schumaker

(57) ABSTRACT

The instant invention is a novel method for definitive pelvic stabilization. The method uses the already established principles of anterior external fixation combined with internal hardware placed in a minimally invasive fashion. Pedicle screws are affixed to the ilia and a rigid, bowed fixation rod is connected between the pedicle screws. Preferably the pedicle screws are attached to the supra-acetabular area of each of the ilium of the pelvis and the fixation rod is bowed anteriorly away from the pelvis.

2 Claims, 6 Drawing Sheets

METHOD FOR MINIMALLY INVASIVE TREATMENT OF UNSTABLE PELVIC RING INJURIES WITH AN INTERNAL ANTERIOR FIXATOR AND POSTERIOR ILIOSACRAL SCREWS

FIELD OF THE INVENTION

The instant invention relates generally to methods and apparatus for the treatment of unstable pelvic fractures. More specifically the invention relates to a method and apparatus for minimally invasive treatment of unstable pelvic ring injuries using an internal anterior fixator and posterior iliosacral screws.

BACKGROUND OF THE INVENTION

Unstable pelvic fractures typically occur as a result of high-energy injuries such as automobile accidents, falls and the like. Even in this age of modern polytrauma care, acute pelvic fractures are potentially lethal. In the past, such injuries were treated without surgery. However, recovery to completely normal functionality was the exception rather than the norm. In more modern times, unstable pelvic fractures are treated surgically with a number of techniques depending on the type and extent of the fracture(s).

The pelvis consists of three major bones (two ilium and the sacrum) and some minor bones joined together in a ring shape and held by strong ligaments, See FIG. 1. General characteristics of pelvic fracture include severe pain, pelvic bone instability, and associated internal bleeding. Devices and methods used to treat fracture of the pelvis currently fall under two general classifications; internal fixation and external fixation. Combinations of both techniques are frequently chosen for certain fracture patterns.

Internal fixation is typically utilized when the patient exhibits unstable posterior pelvic fractures. Internal fixation refers to plates and screws applied directly onto the fracture sites after realignment. See, for example, U.S. Pat. Nos. 4,454,876; 5,108,397; 6,340,362 and 6,440,131. This type of fracture tends to be more complex with it involving multiple bony structures. Internal fixation addresses these clinical issues through open reduction and correction of misaligned bone segments that are subsequently stabilized with a wide variety of plate and screw methods.

Anterior pelvic fractures or hemodynamically unstable patients are candidates for external fixation. Pelvic external fixation consists of pins usually inserted into the iliac bones and then connected together by clamps and bars. See, for example, U.S. Pat. Nos. 4,292,964; 4,361,144; 5,350,378 and 6,162,222. External fixation methods consists of stabilizing the pelvic ring with a rigid framework residing outside the patient's body that is connected to the patient's pelvis via multiple pins that penetrate through the patient's soft and hard tissues. Several frame types are currently utilized. Two of the more widely deployed devices for external pelvic stabilization are the Hoffmann 2 Inverted "A" Frame and the Ganz Pelvic C Clamp.

The application of external reduction and fixation for pelvic fractures is advantageous compared to internal reduction and fixation due to its speed of deployment and lower level of technical training required for utilization. The primary disadvantages of external fixation of pelvic fractures include high risk of pin tract infections, and general patient discomfort. Also, the external frame physically blocks subsequent surgery on the abdomen and they are frequently difficult to fit to obese patients.

The instant inventor has developed a novel method using the already established principles of anterior external fixation. By combining these principles with internal hardware placed in a minimally invasive fashion, this technique allows for definitive pelvic stabilization without having the issues and co-morbidities of an external fixator (i.e. interfering with other procedures, pin care, patient acceptance, later conversion to internal fixation, etc.)

SUMMARY OF THE INVENTION

The present invention comprises a surgical method for minimally invasive treatment of unstable pelvic ring injuries comprising the steps of: affixing at least one fixation means to each ilium of the pelvis; and attaching a rigid, bowed subcutaneous fixation rod to at least one of the fixation means on each ilium.

The fixation means are preferably affixed to the supraacetabular area of each of the ilium of the pelvis. The fixation means preferably is a pedicle screw. The pedicle screw is affixed by: creating a longitudinal incision centered between the Anterior Inferior Iliac Spine (AIIS) and the Anterior Superior Iliac Spine (ASIS); bluntly dissecting through the soft tissues; using fluoroscopic imaging to identify the supraacetabular starting point for the pedicle screw; opening the cortex of the ilium at said starting point with a drill; establishing a corridor between the inner and outer cortices of the ilium using a pedicle finder; and screwing the pedicle screw into the corridor.

The pedicle screw should no not be seated completely to the bone so that the rigid, bowed subcutaneous fixation rod may be passed superficial to the sartorius muscles. The rigid, bowed subcutaneous fixation rod is preferably a titanium rod which may be bowed anteriorly.

The method further comprises subcutaneouslytunneling the anteriorly bowed rod from one of the fixation means on one ilium to another of the fixation means on the other ilium before attaching the rod. Preferably the anteriorly bowed rod is pre-contoured with a bow and cut to the appropriate length before the step of tunneling. The anteriorly bowed rod is preferably positioned with the bow anterior to avoid any potential compressive complications to genitourinary or neurovascular structures prior to said step of attaching said rod. The pelvis should be rotationally and vertically aligned prior to attaching the rod, and preferably prior to tunneling the rod. Compression and tensioning of the pelvis should be performed after attaching said rod. The method further comprises leaving the fixation means and fixation rod attached to the pelvis for 8 to 12 weeks and thereafter removing the fixation means and the rod.

The method may also comprising the further step of stabilizing the posterior instability prior to affixing said fixation means by inserting at least one iliosacral screw through the rear of the ilium and into the sacrum.

DETAILED DESCRIPTION OF THE INVENTION

The instant invention is a novel method for definitive pelvic stabilization. The method uses the already established principles of anterior external fixation combined with internal hardware placed in a minimally invasive fashion. Stabilization of pelvic ring injuries is most often indicated when the volume of the pelvis is increased and/or an unstable pattern of injury is present. This stabilization method must be applied in the operating room under sterile conditions with adequate fluoroscopic guidance. It can be utilized in an emergent setting following provisional stabilization in the emergency room with a pelvic binder, sheet or clamp.

To aid in the determination of utilizing this anterior fixation method, we prefer the Tile classification since it is based on the concept of pelvic stability. In the Tile classification, type A fractures involve a stable pelvic ring. The partially stable type B lesions, such as "open-book" and "bucket-handle" fractures, are caused by external and internal rotation forces, respectively. In type C injuries, there is complete disruption of the posterior sacroiliac complex. These unstable fractures are almost always caused by high-energy severe trauma associated with motor vehicle accidents, falls from a height, or crushing injuries. Type A and type B fractures make up 70% to 80% of all pelvic injuries. This fixation method is typically considered for Tile B and C type injuries. In many patients with partially stable injury patterns, the presence of significant pain with upright posture can be alleviated with the addition of anterior fixation. Supra-acetabular fixation has been shown to have biomechanical advantages compared to iliac crest fixation. If adequate reduction cannot be obtained in a closed manner, then more traditional open reduction techniques need to be employed.

Surgical Technique

The patient may be positioned in the supine position on a radiolucent table. The skin may be prepped and draped from above the umbilicus to the proximal thigh. The lower extremity may be prepped into the field as well to facilitate reduction techniques.

Figure 1:
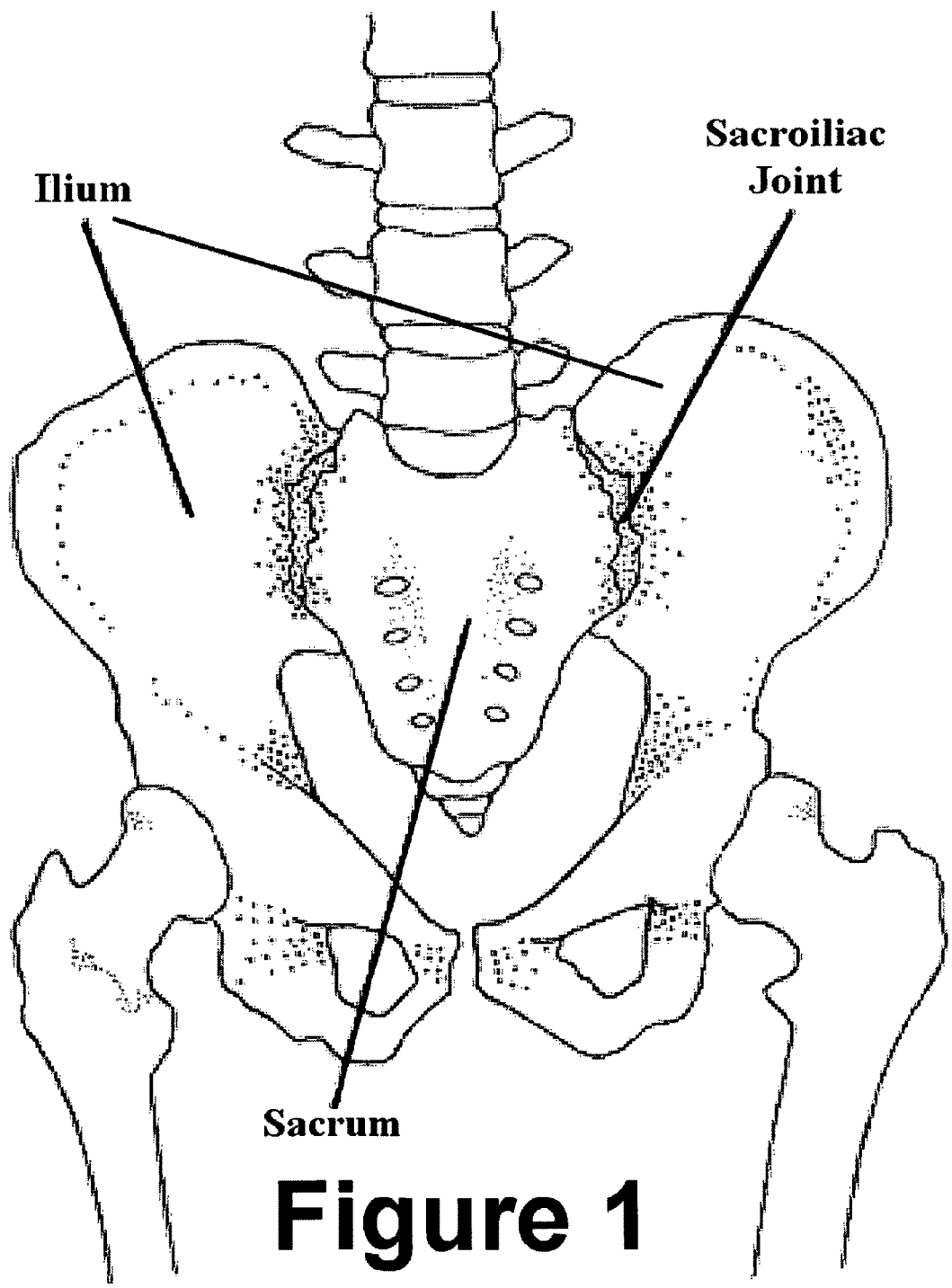
FIG. 1 shows a diagrammatic depiction of a pelvis.
Figure 2:
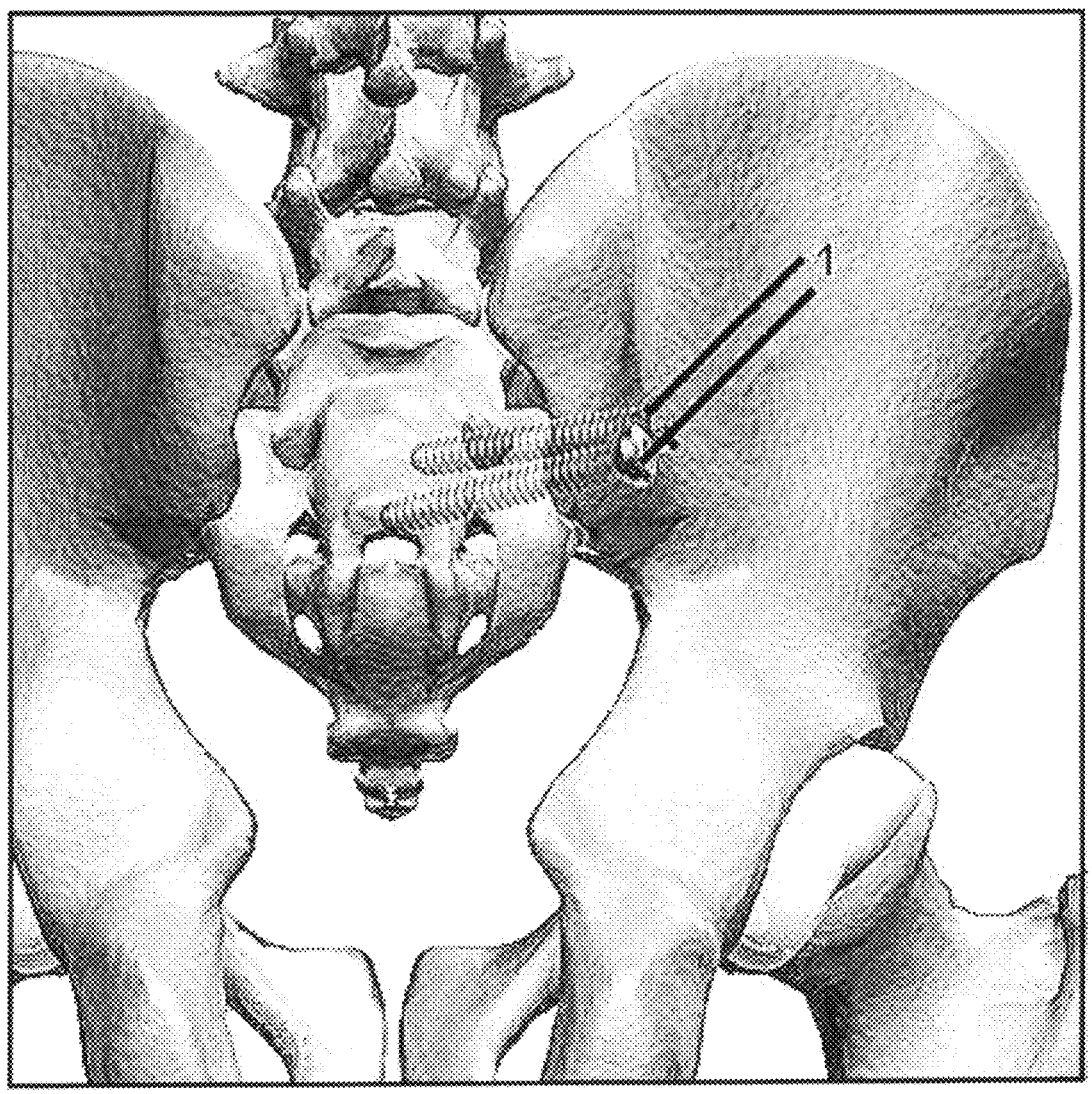
FIG. 2 shows the method in which iliosacral screws are used to perform posterior stabilization of the sacroiliac joint of the pelvis.
Figure 3:
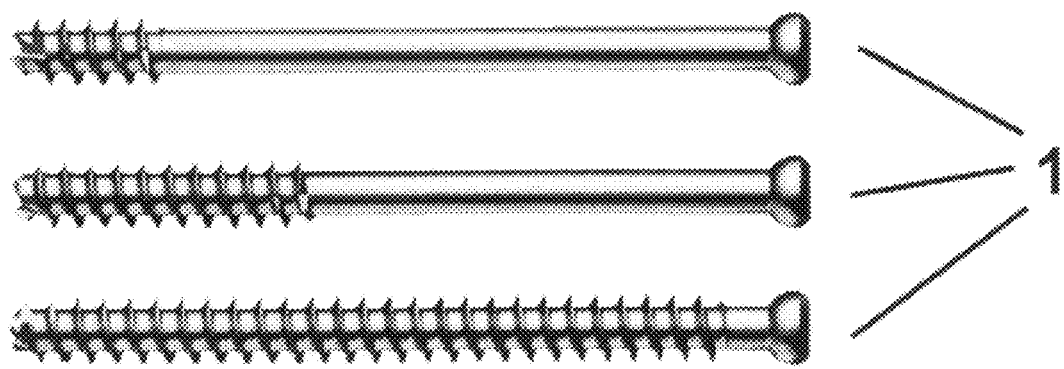
FIG. 3 depicts a variety of iliosacral screws useful for the posterior stabilization of the sacroiliac joint of the pelvis.

The posterior instability may be addressed first. The procedure for placement of iliosacral screws for posterior pelvic instability has been well described and will not be discussed here. See for example "CT-Guided Iliosacral Screw Placement: Technique and Clinical Experience" by Robert L. Sciulli, et al., American Journal of Roentgenology 2007; 188: W181-W192 (reproduced at http://www.ajronline.org/cgi/content/full/188/2/W181). FIG. 2 illustrates the way in which iliosacral screws 1 are inserted through the rear of the ilium and into the sacrum, thus stabilizing the posterior instability. FIG. 3 depicts typical iliosacral screws 1.

After stabilizing the posterior elements via the iliosacral screws, the anterior pelvis may be addressed. A longitudinal incision (preferably 2-3 cm in length) may be made centered between the Anterior Inferior Iliac Spine (AIIS) and the Anterior Superior Iliac Spine (ASIS). Blunt dissection may be used through the soft tissues. Potential dangers in this area include the lateral femoral cutaneous nerve, and care should be taken not to violate the hip capsule. Fluoroscopic imaging may be used to identify the starting point of the supra-acetabular fixation screw. The beam should be directed in an obturator oblique and pelvic outlet direction in order to isolate the appropriate column of bone for screw placement. A recent article by Gardner and Nork describes the appropriate placement of supra-acetabular pins in excellent detail. See "Stabilization of Unstable Pelvic Fractures With Supraacetabular Compression External Fixation", Gardner, et al., Journal of Orthopaedic Trauma 2007; 4:269-273. Once the appropriate starting point is identified, the cortex may be opened with a drill (preferably 5.0 mm). A pedicle finder is then used to establish a corridor between the inner and outer cortices of the ilium. Pedicle screws (preferably USS 8 mm×80 mm) are placed in the supra-acetabular position under fluoroscopic guidance.

Figure 4:
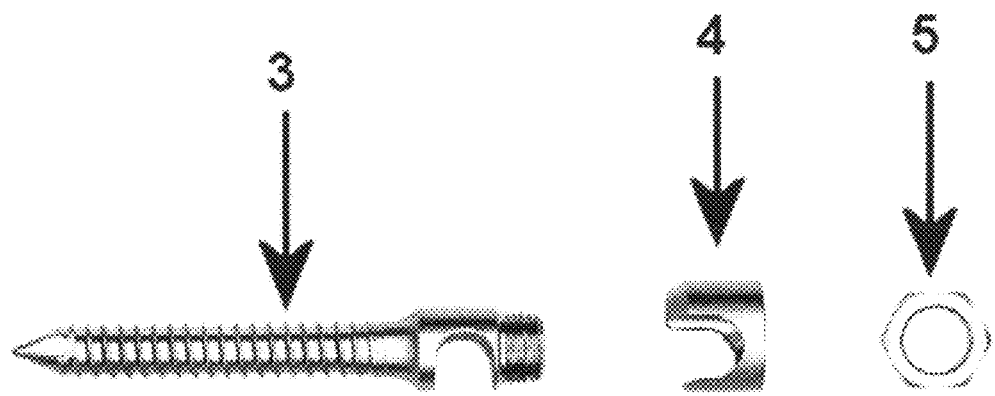
FIG. 4 depicts one embodiment of a pedicle screw system useful in the anterior pelvic stabilization surgical method of the present invention.
Figure 4:
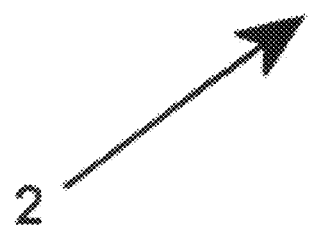
Figure 5:
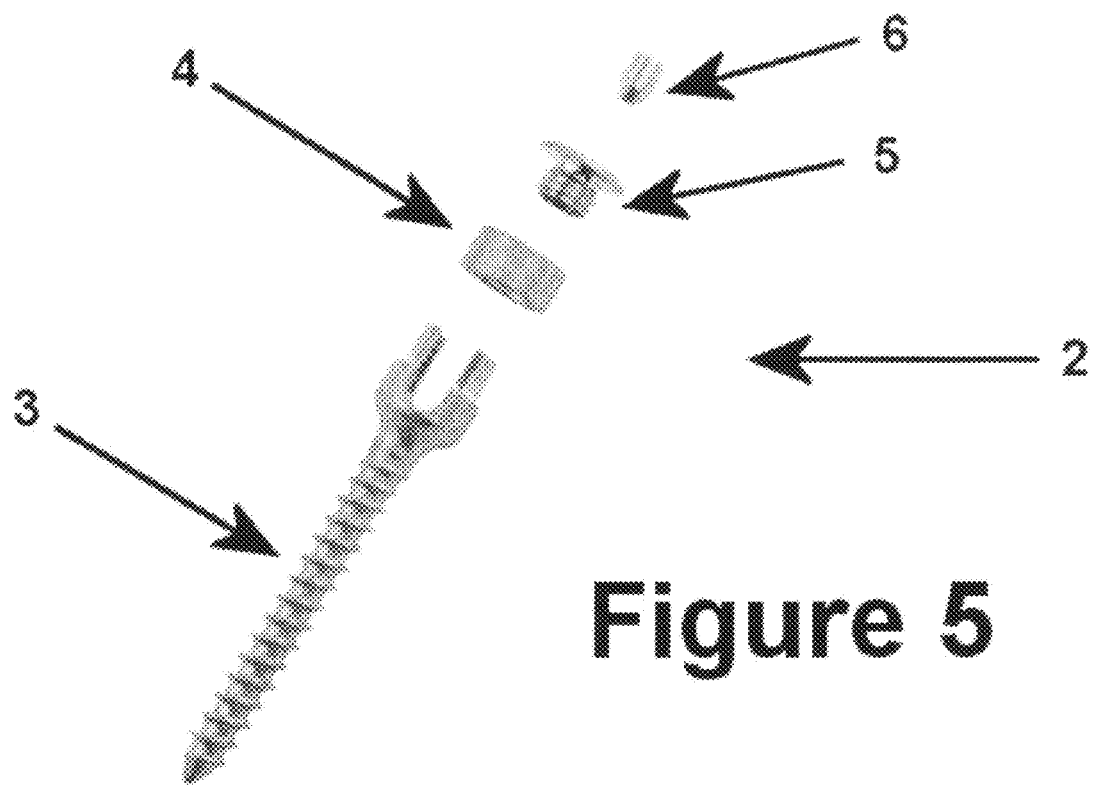
FIG. 5 depicts another embodiment of a pedicle screw system useful in the anterior pelvic stabilization surgical method of the present invention.
Figures 6A, 6B:
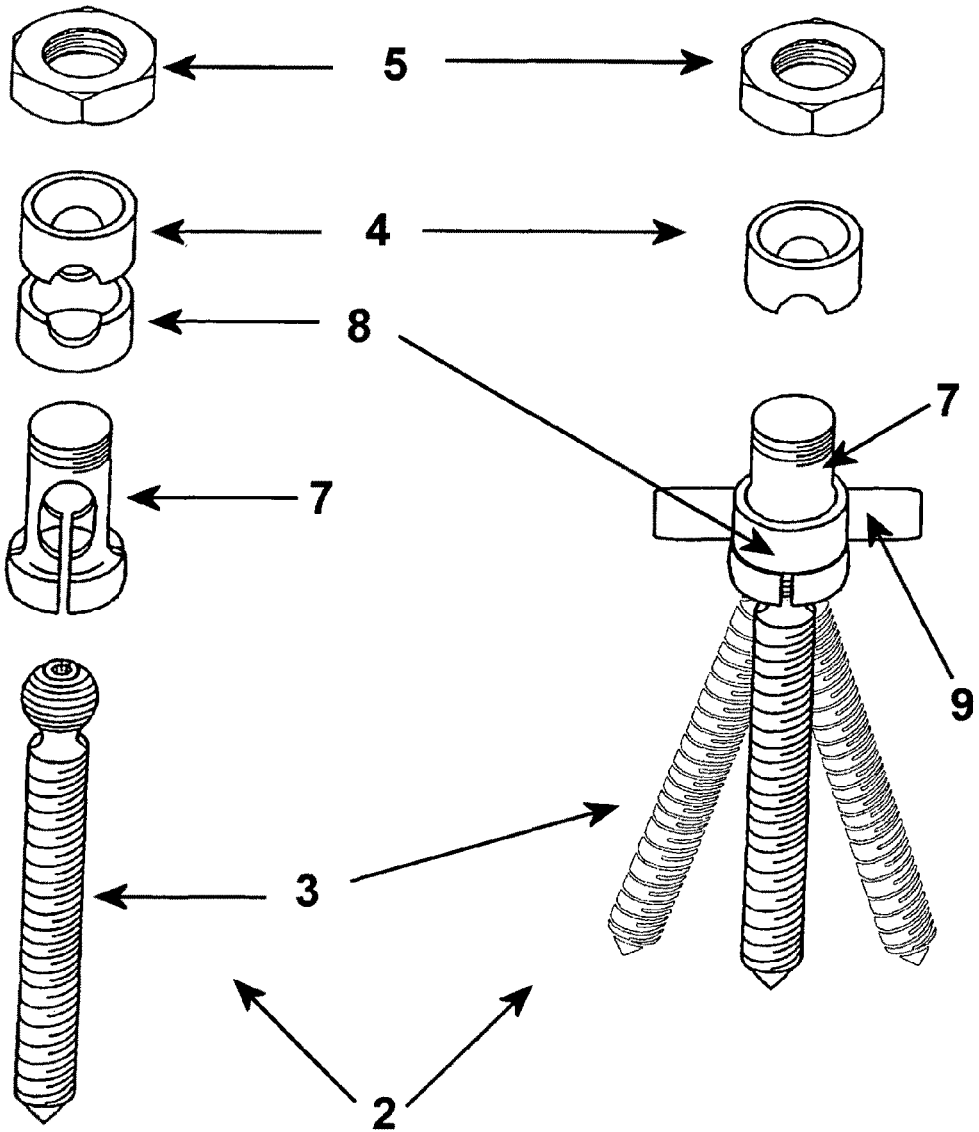
FIGS. 6a and 6b depict yet another embodiment of a pedicle screw system useful in the anterior pelvic stabilization surgical method of the present invention.

FIGS. 4, 5, 6a and 6b show exploded views of three different types of pedicle screw 2 which may be useful in the method of the present invention. Referring to FIG. 4, the separate parts of a side-opening pedicle screw can be seen. Specifically shown are the screw 3, the sleeve 4 and the nut 5. In use, the sleeve 4 and nut 5 are placed over the screw 3 and hold a rod in the cylindrical opening formed by the mating of the screw 3 and the sleeve 4. Turning to FIG. 5, a different type of pedicle screw 2 is seen. In this variety, there is still a screw 3, a sleeve 4 and a nut 5, but there is also a set screw 6 which helps to hold a rod in the opening between the screw 3 and the sleeve 4. Finally, FIGS. 6a and 6b show a polyaxial pedicle screw having a swivel joint. Once again this variety of pedicle screw has a screw 3, a sleeve 4 and a nut 5, but this type also has a mechanism consisting of a swivel clamp 7 and a swivel clamp collar 8. This added hardware allows the head of the pedicle screw to swivel somewhat independently from the screw 3. Thus this swivel head allows for ease of fit to curved rods 9 without the requirement for excessive rod contouring.

Returning to the surgical method, it should be noted that the screws are preferably not seated completely to the bone so that the connecting rod may be passed superficial to the sartorius muscles. A titanium rod 9 (preferably USS 6 mm) may then be pre-contoured with a bow, placed over the screws 2 and cut to the appropriate length on the back table. The rod may preferably be anywhere from 6 mm to 1 cm in diameter and may also be pre-bent for ease of use. The rod may then be tunneled subcutaneously from one screw to the other. Before connecting the rod, it may be positioned with the bow anterior to avoid any potential compressive complications to genitourinary or neurovascular structures. Also, any necessary reduction may be performed at this stage. Rotational and vertical alignment should be performed prior to attaching the rod, and preferably prior to tunneling the rod to limit pressure on the soft tissues. If posterior fixation is used, then most of the reduction should be complete at this point. This hardware system allows for compression and tensioning once the rod is in place. Reduction and hardware position may be assessed on fluoroscopic AP, inlet and outlet views. As an alternative to fluoroscopic AP, CT guidance may be used. The construct is intended as definitive treatment, with removal typically performed after 8 to 12 weeks. The timing of application and removal is ultimately determined on an individual case basis.

Figure 7:
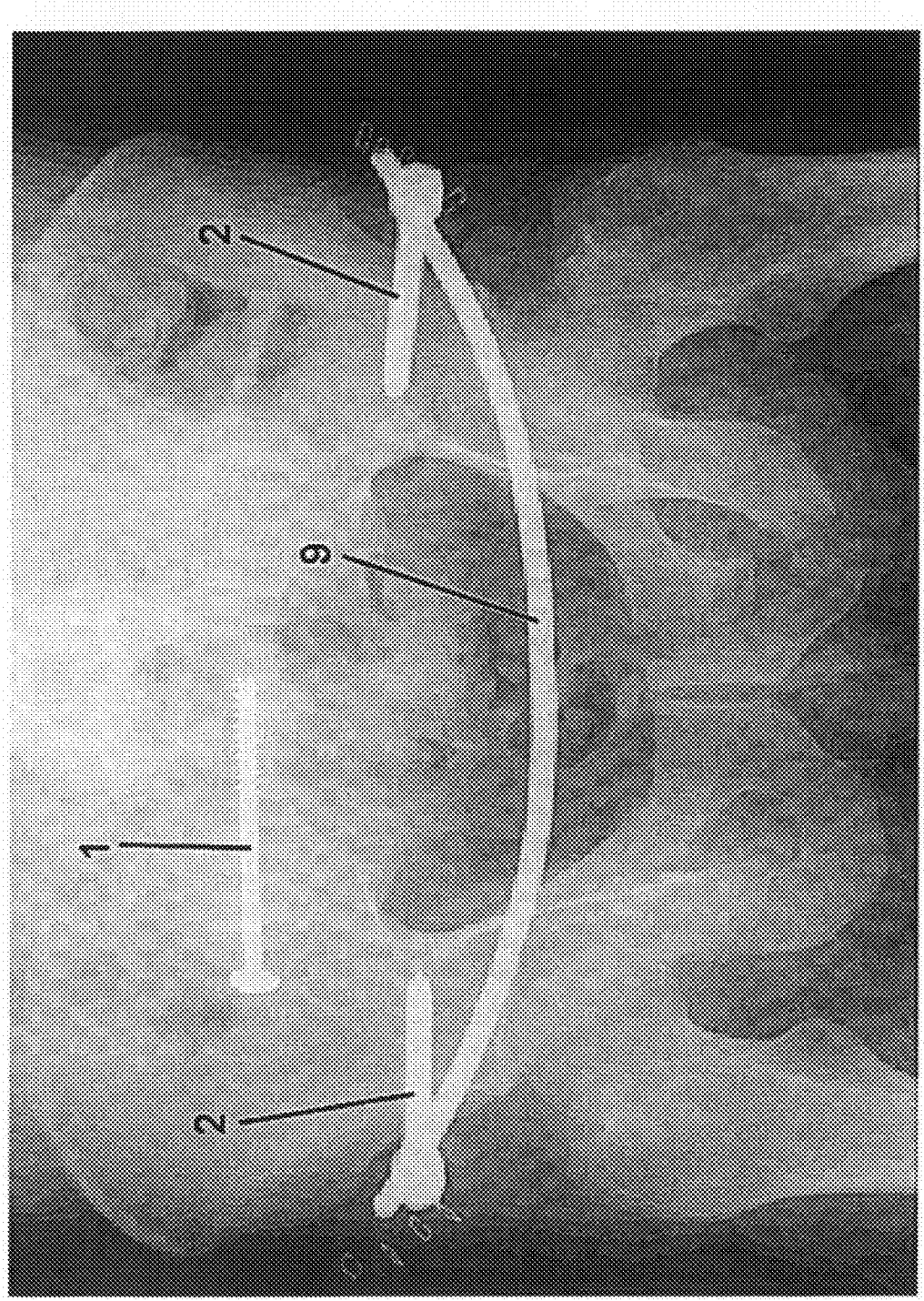
FIG. 7 is an x-ray of a patient who has had posterior stabilization of the sacroiliac joint of the pelvis using an iliosacral screw as well as the anterior stabilization surgical method of the present invention using two pedicle screws and an anteriorly bowed rod.

FIG. 7 shows an x-ray of a 32-year old male who was involved in a motor vehicle accident and upon whom the inventive surgical method was performed. As can be seen, the posterior was stabilized and fixated using an iliosacral screw 1. The anterior was fixated and stabilized by the inventive method using two pedicle screws 2, one attached to the supraacetabular portion of each ilium. Connected between the pedicle screws 2 is a rigid, anteriorly bowed subcutaneous fixation rod 9.

The biomechanical stability of the inventive supra-acetabular pedicle screw internal fixation construct was evaluated and compared with the more prevalent external fixator. Three different pedicle screw constructs were compared to the external fixator, a mono axial screw system and two different polyaxial screw systems.

A total of 4 constructs were tested. These included: 1) an external fixation system; 2) a mono-axial pedicle screw system; 3) a polyaxial pedicle screw system (Click'X, a trademark of Synthes Inc., West Chester Pa.); and 4) another polyaxial pedicle screw system (Pangea, a trademark of Synthes Inc., West Chester Pa.). All constructs were assembled to have an active length of the longitudinal element equal to 280 mm. For the pedicle screws systems, screws were inserted into the test blocks, leaving an approximate 15 mm gap between screw head and test block. This resulted in a construct moment arm of 75 mm. The external fixator constructs were assembled with a 145 mm construct moment arm as this is where the fixator connection was measured to lie in a clinical setting.

Test Apparatus 1) an MTS RT/50 Electromechanical Test Frame, from MTS Corp. (Eden Praire, Minn.), Calibrated: February 2008; and 2) an MTS Bionix Electromechanical Torsion Test Frame, from MTS Corp. (Eden Praire, Minn., Calibrated: March 2008.

Test Procedure

All constructs were tested first in axial compression. Loads were applied in the elastic range (20 mm displacement). Once axial testing was completed, 3 components were tested in torsion, within the elastic range (10°), and 2 were to failure. The three components tested within the elastic range (axial and torsion) were then retested in axial compression until failure.

Axial Testing: Standard clevis fixtures were rigidly attached to the load cell and lower platen of the test machine. Constructs were mounted to the clevis fixtures using 12.7 mm diameter steel hinge pins.

An axial tensile load was applied to the construct at a test speed of 5 mm/min. Load-displacement curves were acquired for each construct tested and bending yield load, stiffness and ultimate bending failure load were calculated, as applicable. Yield load will calculation are based upon 0.020×the active length (5.6 mm). Note: testing was performed for a maximum of 75 mm of axial displacement. Results are shown in Table 1.

Torsion Testing: Clevis fixtures that prevented rotation of the test block were rigidly attached to the load cell and lower plate of the test machine. Constructs were mounted to the clevis fixtures using 12.7 mm diameter steel hinge pins. Spacers, that prevent test block rotations about the hinge pins, were manually set.

An angular displacement was applied to the construct at a test speed of 60°/min. Axial load was maintained at 0 Newton. Torque-angular displacement curves were acquired for each construct tested and torsional yield load, stiffness and ultimate torque will be calculated, as applicable. Yield torque was based upon a 5° offset. Note: testing was performed for a maximum of 60° or angular rotation. Results are shown in Table 2.

TABLE 1

Summary Results - Axial

| Type | Peak Load (N) | Yield Load (N) | Bending Stiffness (N/mm)* | p-value (vs. Ex Fix) |
|---|---|---|---|---|
| External Fixator | 160 ± 4 | 102 ± 3 | 2.88 ± 0.05 | — |
| USS Monoaxial | 370 ± 15 | *** | 4.01 ± 0.11 | >0.0001 |
| Click'X Polyaxial | 158 ± 1 | *** | 3.64 ± 0.11 | >0.0001 |
| Pangea Polyaxial | 137 ± 1 | *** | 3.63 ± 0.15 | >0.0001 |

TABLE 2

Summary Results - Torsional

| Type | Peak Torque (N-mm) | Yield Torque (N-mm) | Torsional Stiffness (N-mm/°)* | p-value (vs. Ex Fix) |
|---|---|---|---|---|
| External Fixator | 14.70 | 4.92 | 0.50 ± 0.07 | — |
| USS Monoaxial | 5.94 | 4.47 | 0.38 ± 0.01 | 0.0163 |
| Click'X Polyaxial | 6.93 | 4.40 | 0.38 ± 0.04 | 0.0124 |
| Pangea Polyaxial | 6.99 | 5.26 | 0.38 ± 0.01 | 00055 |

The results show that the construct of pedicle screws is superior to the external fixator in axial loading. However, the torsional stiffness is greater with the external fixator.

It is to be expected that considerable variations may be made in the embodiments disclosed herein without departing from the spirit and scope of this invention. Particularly, while the invention has been described with respect to pedicle screws 2 that have been attached to the anterior of each ilium and the bowed fixation rod 9 has been bowed anteriorly away from the pelvis, the invention can alternatively call for the attachment of the pedicle screws 2 to the posterior of the ilia and the bowed fixation rod 9 can be bowed posteriorly away from the pelvis. Accordingly, the significant improvements offered by this invention are to be limited only by the scope of the following claims.

I claim:

1. A surgical method for minimally invasive treatment of unstable pelvic ring injuries comprising the steps of:
   providing at least two fixation means and a bowed subcutaneous fixation rod, said bowed subcutaneous fixation rod having a first end and a second end;
   affixing a first of said at least two fixation means to a first ilium of the pelvis and a second of said at least two fixation means to the second ilium of the pelvis;
   subcutaneously tunneling said subcutaneous fixation rod from one of said at least two fixation means on one ilium to another of said at least two fixation means on the other ilium;
   attaching said first end of said bowed subcutaneous fixation rod to said first of said at least two fixation means;
   attaching said second end of said bowed subcutaneous fixation rod to said second of said at least two fixation means.

2. The surgical method of claim 1, wherein said fixation means are attached to the supra-acetabular area between the Anterior Inferior Iliac Spine (AIIS) and the Anterior Superior Iliac Spine (ASIS) of each of the ilium of the pelvis; and said bowed subcutaneous fixation rod is tunneled in a subcutaneous arc from said first fixation means to said second fixation means and said bowed subcutaneous fixation rod does not arc inferior to a line between the Anterior Inferior Iliac Spine (AIIS) of each ilium and does not arc superior to a line between the Anterior Superior Iliac Spine (ASIS) of each ilium.

* * * * *